US004001787B2

United States Statutory Invention Registration [19]

[11] Reg. Number: H1787

Ogasawara et al. [45] Published: Feb. 2, 1999

[54] REGENERATION METHOD OF WORKING SOLUTION

[76] Inventors: Kazuharu Ogasawara, c/o Mitsubishi Gas Chemical Company Inc., Kashima Factory, Towada 35, Kamisu-machi, Kashima-gun, Ibaraki-ken; Tomio Kato; Kazuyuki Minato, both of c/o Mitsubishi Gas Chemical Company, Inc., Tokyo Research Laboratory, 1-1, Niijuku 6-chome, Katsushika-ku, Tokyo; Kenji Kato, c/o Mitsubishi Gas Chemical Company, Inc., Tokyo Research Laboratory, 1-1, Niijuku 6-chome, Katsushika-ku, Tokyo; Makoto Sumitani, c/o Mitsubishi Gas Chemical Company, Inc., Tokyo Research Laboratory, 1-1, Niijuku 6-chome, Katsushika-ku, Tokyo, all of Japan

[21] Appl. No.: 829,696

[22] Filed: Mar. 26, 1997

[30] Foreign Application Priority Data

Apr. 12, 1996 [JP] Japan ..... 8-091238
Apr. 12, 1996 [JP] Japan ..... 8-091239

[51] Int. Cl.[6] ..... C07D 50/18
[52] U.S. Cl. ..... 552/208
[58] Field of Search ..... 552/269; 423/588

[56] References Cited

U.S. PATENT DOCUMENTS

| | | | |
|---|---|---|---|
| 2,739,875 | 3/1956 | Sprauer et al. | 260/369 |
| 3,432,267 | 3/1969 | Lee et al. | 23/207 |
| 3,752,885 | 8/1973 | Liebert et al. | 423/588 |
| 3,880,596 | 4/1975 | Liebert et al. | 23/283 |
| 3,965,251 | 6/1976 | Shin et al. | 423/588 |
| 4,566,998 | 1/1986 | Ochoa et al. | 260/369 |
| 5,399,333 | 3/1995 | Kato et al. | 423/588 |

FOREIGN PATENT DOCUMENTS 2003268 7/1971 Germany .

OTHER PUBLICATIONS

Sandelin, Fredrik, et al., "Kinetics of the Catalys Deactivation in the Recovery of Active Anthraquinones", *Catalyst Deactivation (1994),Studies in Surface Science and Catalysis*, vol. 88, 635–640 (1994).

*Primary Examiner*—Charles T. Jordan
*Assistant Examiner*—Meena Chelliah

[57] ABSTRACT

A regeneration method of a working solution is herein disclosed in which various by-products which do not participate in the production of hydrogen peroxide and which are present in the working solution in a hydrogen peroxide production process utilizing an anthraquinone method can efficiently be converted into anthraquinones effective as reaction media for the production of hydrogen peroxide.

The present invention is concerned with (1) a regeneration method of a working solution wherein at least a part of the unreduced working solution is brought into contact with a catalyst mainly comprising a γ-alumina at a temperature of 40 to 150° C., and (2) another regeneration method of a working solution wherein the working solution is brought into contact with a catalyst mainly comprising a γ-alumina at a temperature of 20 to 150° C. under conditions that a concentration h (mol/liter) of the alkyltetrahydroanthrahydroquinones in the working solution before the catalytic treatment meets the equation $$(0.0018 \times t - 0.0285) \times h < 0.05$$

wherein t is a treatment temperature (°C.), to convert alkyltetrahydrooxyanthrones in the working solution into the alkyltetrahydroanthrahydroquinones.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

REGENERATION METHOD OF WORKING SOLUTION

BACKGROUND OF THE INVENTION

1. Field of the Invention

The present invention relates to a regeneration method of a working solution in a hydrogen peroxide production process. More specifically, the present invention relates to a regeneration method of a working solution by which various by-products which do not participate in the production of hydrogen peroxide and which are present in the working solution in a hydrogen peroxide production process utilizing an anthraquinone method can efficiently be converted into anthraquinones effective as reaction media for the production of hydrogen peroxide.

2. Description of the Related Art

A main production process of hydrogen peroxide which has currently been practiced on an industrial scale is called an anthraquinone method in which anthraquinones are used as reaction media. In general, the anthraquinones are used by dissolving them in an appropriate organic solvent. This organic solvent may be a single organic solvent or a mixed organic solvent, but it is usually a mixture of two organic solvents. The solution obtained by dissolving the anthraquinones in the organic solvent is called "a working solution".

According to the anthraquinone method, the anthraquinones in the working solution are subjected to reduction (hereinafter referred to as "the hydrogenation") with hydrogen in the presence of a catalyst in a reduction step to produce corresponding anthrahydroquinones. Next, in an oxidation step, the anthrahydroquinones are oxidized with air or an oxygen-containing gas to convert the anthrahydroquinones into the anthraquinones again and to simultaneously produce hydrogen peroxide. Hydrogen peroxide produced in the working solution is usually extracted with water in an extraction step to be separated from the working solution. The working solution from which hydrogen peroxide has been separated is returned to the reduction step again, thereby forming a cyclic process. This cyclic process can produce hydrogen peroxide substantially from hydrogen and air, and hence it is an extremely efficient process. This cyclic process has already been used for the industrial production of hydrogen peroxide.

In the hydrogen peroxide production process utilizing the anthraquinone method, the anthraquinones contained as the reaction media in the working solution are reduced into the anthrahydroquinones, and they are further oxidized to produce the anthraquinones and hydrogen peroxide. While this procedure is repeated, alkyloxyanthrones, alkyltetrahydroanthraquinone epoxides and the like are produced by side reactions. These alkyloxyanthrones, alkyltetrahydroanthraquinone epoxides and the like cannot produce hydrogen peroxide, even when repeatedly subjected to the reduction and oxidation. The production of these useless compounds is very small per occurrence of the reduction and oxidation, but while the circulation is repeated, the above-mentioned compounds are accumulated in the working solution and cause various troubles.

If the nuclei of the alkylanthraquinones are hydrogenated, the alkyltetrahydroanthraquinones are produced, but these alkyltetrahydroanthraquinones have an ability of producing hydrogen peroxide by the repetition of the reduction and oxidation like the alkylanthraquinones. However, the alkyltetrahydroanthraquinones can easily be obtained by reducing the alkylanthraquinones, but the alkyltetrahydroanthraquinones obtained by the reduction have a drawback that their oxidation rate is low. Therefore, as indicated by German Patent No. 2003268, in the case that the alkyltetrahydroanthraquinones are used as the media for the reduction and oxidation, an extremely large energy is required in the oxidation step, and hence half or more of the total energy required in a circulation process is consumed in the oxidation step, which leads to problems regarding apparatus and economy. As one means for solving these problems, for example, in U.S. Pat. No. 5,399,333, ratios of the reduction and oxidation between the alkylanthraquinones and the alkyltetrahydroanthraquinones can be controlled in a suitable range to obtain an economically advantageous process. However, when the alkyltetrahydroanthraquinones gradually increase and the ratios of the reduction and oxidation increase, the above-mentioned problems regarding the apparatus and economy similarly arise.

In view of the above-mentioned problems, in the hydrogen peroxide production process utilizing the anthraquinone method, there is required a step in which the alkyltetrahydroanthraquinones and the alkylanthraquinones are regenerated from compounds such as the alkyltetrahydroanthraquinone epoxides and the alkyloxyanthrones and which cannot produce hydrogen peroxide, and a step in which the alkylanthraquinones are regenerated from the alkyltetrahydroanthraquinones. Thus, many suggestions have been made so far.

In Japanese Patent Publication No. 8806/1964, it has been suggested that inert components are converted into the alkyltetrahydroanthraquinones by treating the working solution with an alkali and an aqueous alkali solution. Furthermore, in Japanese Patent Publication No. 11658/1968, it has been reported that the reduced working solution is treated with caustic soda or sodium silicate at 120° C. to regenerate the alkyltetrahydroanthraquinone epoxides. However, when the working solution in which a part of the anthraquinones are present as the anthrahydroquinones obtained by their reduction is brought into contact with an aqueous alkali solution, the anthrahydroquinones are extracted with the aqueous alkali solution, which leads to an economical problem, i.e., the loss of the expensive anthraquinones.

Japanese Patent Publication No. 19164/1970 has reported that the regeneration of the working solution can be accomplished by treating the working solution with ozone, further treating it with an aqueous caustic soda solution, and then passing it through active alumina at 70 to 75° C. However, this regeneration method comprises 3 steps and it is complicated, and since expensive ozone is used, problems regarding economy and an apparatus are present.

Japanese Patent Publication No. 41040/1974 has suggested a method for regenerating the alkyloxyanthrones by treating the working solution at 130° C. in the presence of a catalyst supporting palladium by the use of an olefin, but a large amount of the olefin and the expensive platinum group metal are used in this method. For these reasons, this method is also considered to be an economically disadvantageous process.

Furthermore, as a method for converting the alkyltetrahydroanthraquinones into the alkylanthraquinones, Japanese Patent Publication No. 4474/1964 has reported that the alkyltetrahydroanthraquinones can be converted into the alkylanthraquinones by bringing alumina, magnesia, a spinel of magnesia-alumina, carbon, or a metal having a hydrogenation ability such as palladium, platinum or nickel into contact with the working solution and a compound having an unsaturated bond such as an olefin. Also in this case, however, in order to heighten a reaction rate, a large amount of the olefin is used and the employment of the expensive platinum group metal is required. Hence, the reported method is also considered to be an economically disadvantageous process.

As understood from the foregoing, the regeneration methods of the working solution by the conventional techniques have some problems regarding an apparatus and economy. For example, a plurality of steps are required and so the operation is intricate, or the addition of a compound other than the catalyst is necessary, or the anthraquinones are probably lost in a certain ratio.

Furthermore, in the conventional techniques, it has not been solved that the alkylanthraquinones and the alkyltetrahydroanthraquinones are regenerated from the alkyloxyanthrones and the alkyltetrahydroanthraquinone epoxides and simultaneously the alkyltetrahydroanthraquinones are converted into the alkylanthraquinones.

On the other hand, the present inventors have found that, in the case that the working solution containing at least the alkyltetrahydroanthraquinones as the anthraquinones is repeatedly reduced and oxidized to produce hydrogen peroxide, alkyltetrahydrooxyanthrones are accumulated in the working solution. The alkyltetrahydrooxyanthrones do not produce hydrogen peroxide, even when repeatedly subjected to the reduction and oxidation, and therefore, the alkyltetrahydrooxyanthrones accumulated in the working solution by repeating the circulation inconveniently cause various troubles. In addition, this fact leads to the loss of the anthraquinones effective to produce hydrogen peroxide, which is economically disadvantageous. The present inventors have found that when the reduced working solution is treated with a catalyst such as alumina with a view to particularly regenerate the alkyltetrahydroanthraquinone epoxides, the concentration of the alkyltetrahydrooxyanthrones increases. For the purpose of solving this problem, in the hydrogen peroxide production process utilizing the anthraquinone method, it is necessary that the alkyltetrahydroanthraquinones should be regenerated from the alkyltetrahydrooxyanthrones.

As the conventional techniques regarding the regeneration method of the working solution, in addition to the above-mentioned techniques, there have been reported a production method of a desired compound from the alkyltetrahydroanthraquinone epoxides in Japanese Patent Publication No. 30801/1982, and a method for regenerating the alkylanthraquinones from the alkyltetrahydroanthraquinones in "Studies in Surface Science and Catalysis", Vol. 88, p. 635 (1994).

In these conventional techniques, however, the regeneration from the alkyltetrahydrooxyanthrones in the working solution has not been described at all.

SUMMARY OF THE INVENTION

In view of such circumstances, the present invention has now been developed, and the first object of the present invention is to provide a regeneration method of a working solution in a hydrogen peroxide production process utilizing an anthraquinone method which comprises the step of converting alkyloxyanthrones and alkyltetrahydroanthraquinones in the working solution into alkylanthraquinones, and converting alkyltetrahydroanthraquinone epoxides in the working solution into alkyltetrahydroanthraquinones.

The second object of the present invention is to provide a regeneration method of a working solution in a hydrogen peroxide production process utilizing an anthraquinone method which comprises the step of converting alkyltetrahydrooxyanthrones in the working solution into alkyltetrahydroanthrahydroquinones.

The present inventors have intensively researched to achieve the above-mentioned objects. As a result, it has been found that the first object of the present invention can be achieved by bringing at least a part of an unreduced working solution into contact with a catalyst mainly comprising a γ-alumina at a specific temperature. Furthermore, the second object of the present invention can be achieved by bringing a working solution containing alkyltetrahydroanthrahydroquinones at a specific concentration into contact with a catalyst mainly comprising a γ-alumina at a specific temperature.

The present invention has been completed on the basis of the above-mentioned findings.

That is to say, the first object of the present invention can be achieved by a regeneration method of a working solution which comprises the step of repeatedly reducing and oxidizing the working solution containing alkylanthraquinones and alkyltetrahydroanthraquinones as anthraquinones to produce hydrogen peroxide, wherein at least a part of the unreduced working solution is brought into contact with a catalyst mainly comprising a γ-alumina at a temperature of 40° to 150° C. (the first invention).

The second object of the present invention can be achieved by a regeneration method of a working solution which comprises the step of repeatedly reducing and oxidizing the working solution containing at least alkyltetrahydroanthraquinones as anthraquinones to produce hydrogen peroxide, wherein the working solution is brought into contact with a catalyst mainly comprising a γ-alumina at a temperature of 20° to 150° C. under conditions that a concentration h (mol/liter) of the alkyltetrahydroanthrahydroquinones in the working solution before the catalytic treatment meets the equation $$(0.0018\times t-0.0285)\times h<0.05$$

wherein t is a treatment temperature (°C.), to convert alkyltetrahydrooxyanthrones in the working solution into the alkyltetrahydroanthrahydroquinones (the second invention).

DETAILED DESCRIPTION OF THE PRESENT INVENTION

A working solution which can be applied to a method of the present invention is a solution containing anthraquinones as reaction media or anthrahydroquinones which are their hydrides, and this solution can be used as a circulating solution in a hydrogen peroxide production process utilizing an anthraquinone method.

In the hydrogen peroxide production process utilizing the anthraquinone method, the working solution containing the anthraquinones as the reaction media is first reduced in a reduction step with hydrogen to hydrogenate the anthraquinones in the working solution, whereby corresponding anthrahydroquinones are produced. Next, this reduced solution is oxidized in an oxidation step with an oxygen-containing gas to convert the anthrahydroquinones into the corresponding anthraquinones again and to simultaneously produce hydrogen peroxide. Hydrogen peroxide in the working solution is extracted in an extraction step usually with water to separate it from the working solution. The working solution from which hydrogen peroxide has been separated is returned to the reduction step again. As understood from the foregoing, by the repetition of the reduction and oxidation treatment of the anthraquinones, hydrogen peroxide can continuously be produced from hydrogen and air.

No particular restriction is put on a solvent for use in the preparation of the working solution which can be used in this hydrogen peroxide production process, but examples of the preferable solvent include a combination of an aromatic hydrocarbon and a higher alcohol, a combination of an aromatic hydrocarbon and a carboxylic acid ester of cyclohexanol or an alkylcyclohexanol, and a tetrasubstituted urea. A combination of trimethylbenzene and diisobutylcarbinol is particularly preferable.

Furthermore, as the anthraquinones which are the reaction media, alkylanthraquinones and alkyltetrahydroanthraquinones can be used. Here, examples of the alkyltetrahydroanthraquinones include amyltetrahydroanthraquinone, ethyltetrahydroanthraquinone, t-butyltetrahydroanthraquinone and mixtures thereof. In addition, examples of the alkylanthraquinones include amylanthraquinone, ethylanthraquinone, t-butylanthraquinone and mixtures thereof.

In the first place, the first invention will be described.

In the first invention, the working solution containing the alkylanthraquinones and the alkyltetrahydroanthraquinones can be used. In this case, the alkylanthraquinones may be used singly or in a combination of two or more thereof. Furthermore, the alkyltetrahydroanthraquinones may also be used singly or in a combination of two or more thereof.

In the first invention, the unreduced working solution is used. If the reduced working solution is used, the rate of regenerating the alkylanthraquinones from the alkyltetrahydroanthraquinones inconveniently lowers, and what is worse, other by-products are liable to be produced in large quantities.

Preferable examples of the unreduced working solution include a solution containing 0.05 mol/liter or more of the alkyltetrahydroanthraquinones, a solution containing 0.15 mol/liter or less of alkyltetrahydroanthrahydroquinones and a solution containing 0.05 mol/liter or more of the alkyltetrahydroanthraquinones and 0.15 mol/liter or less of the alkyltetrahydroanthrahydroquinones.

In the first invention, at least a part of the unreduced working solution is brought into contact with the catalyst mainly comprising a γ-alumina. This catalyst mainly comprising the γ-alumina has a high activity and is economically advantageous. No particular restriction is put on the particle size of the catalyst, but it is preferably in the range of 8 to 100 mesh. If the particle size is less than this range, a pressure loss in a reactor inconveniently increases, and on the other hand, if it is larger than the above-mentioned range, the catalytic activity inconveniently deteriorates.

No particular restriction is put on the kind of γ-alumina, and the commercially available γ-alumina can usually widely be used. Furthermore, in the present invention, there can also be used a catalyst comprising this γ-alumina and about 10 wt% or less of calcium oxide, magnesium oxide, copper oxide, or a substance mainly consisting of them, for example, $CaO \cdot Al_2O_3$ or $MgO \cdot Al_2O_3$.

In the present invention, the unreduced working solution is brought into contact with the catalyst mainly comprising the γ-alumina, but in this case, a catalytic treatment temperature is selected in the range of 40° to 150° C. If this temperature is less than 40° C., a reaction rate is so low as to be impractical, and on the other hand, if it is more than 150° C., useless reactions other than an intended regeneration reaction easily occur. In addition, a catalytic treatment time depends upon the kind of catalyst and the catalytic treatment temperature, and it cannot be decided sweepingly, but it is usually in the range of about 10 to 120 minutes. Moreover, no particular restriction is put on the type of a reactor which can be used in this catalytic treatment, and any of a stirrer-equipped type, a fixed bed type and a fluidized bed type can be used.

As described above, when the unreduced working solution is simply regenerated by the use of the simple apparatus and the inexpensive catalyst, the alkyloxyanthrones and the alkyltetrahydroanthraquinone contained in the working solution can efficiently be converted into alkylanthraquinones, and the alkyltetrahydroanthraquinone epoxides contained in the working solution can efficiently be converted into the alkyltetrahydroanthraquinones without losing the effective anthraquinones.

Next, the second invention will be described.

In the second invention, the working solution containing at least the alkyltetrahydroanthraquinones is used, but the working solution containing a mixture of the alkyltetrahydroanthraquinones and the alkylanthraquinones is particularly preferable. In this case, the alkyltetrahydroanthraquinones may be used singly or in a combination of two or more thereof. Moreover, the alkylanthraquinones may be used singly or in a combination of two or more thereof.

In this second invention, either of the unreduced working solution and the reduced working solution can be used. As the catalyst which is brought into contact with this working solution, the catalyst mainly comprising a γ-alumina can be used, but this catalyst may be the same as described in the first invention.

In the second invention, the working solution is brought into contact with the catalyst mainly comprising the γ-alumina at a temperature of 20° to 150° C. under conditions that a concentration h (mol/liter) of the alkyltetrahydroanthrahydroquinones in the working solution before the catalytic treatment meets the equation $$(0.0018 \times t - 0.0285) \times h < 0.05$$

wherein t is a treatment temperature (°C.), to convert alkyltetrahydrooxyanthrones in the working solution into the alkyltetrahydroanthrahydroquinones. In this case, as the concentration of the alkyltetrahydroanthrahydroquinones in the working solution is low, the concentration of the alkyltetrahydrooxyanthrones in the regenerated working solution can be lowered. Furthermore, as the temperature is low, the concentration of the alkyltetrahydrooxyanthrones in the regenerated working solution can be lowered. However, if the temperature is less than 20° C., a reaction rate is so low as to be impractical. The preferable treatment conditions are that the treatment temperature is in the range of 20° to 150° C. and the concentration h (mol/liter) of the alkyltetrahydroanthrahydroquinones in the working solution before the catalytic treatment is 0.15 mol/liter or less and meets the equation $$(0.0018 \times t - 0.0285) \times h < 0.02$$

wherein t is a treatment temperature (°C.).

The concentration of the alkyltetrahydroanthrahydroquinones in the working solution can be adjusted suitably by oxidizing the working solution. Moreover, no particular restriction is put on the type of a reactor which can be used in this catalytic treatment, and any of a stirrer-equipped type, a fixed bed type and a fluidized bed type can be used.

When the working solution is regenerated under such conditions, the alkyltetrahydrooxyanthrones in the working solution can efficiently be converted into the alkyltetrahydroanthrahydroquinones.

Next, the present invention will be described in more detail, but the scope of the present invention should not be limited to these examples.

EXAMPLE 1

Amyltetrahydroanthraquinone was dissolved in a mixed solvent of 60 vol% of 1,2,4-trimethylbenzene and 40 vol% of diisobutylcarbinol to prepare a working solution in which the concentration of amyltetrahydroanthraquinone was 0.225 mol/liter, and the working solution was then sufficiently oxidized to regulate, to 0.000 mol/liter, the concentration of anthrahydroquinones which were reductants. In this example, AA400G (14 to 48 mesh) made by Alcan Chemicals Co., Ltd. was used as a γ-alumina. Next, 100 ml of the above-mentioned working solution was placed in a 200-ml flask, and the introduction of nitrogen was begun and the working solution was then heated up to 120° C. with stirring. When the working solution had reached 120° C., 10.0 g of the γ-alumina was fed, and reaction was carried out for 1 hour. A reaction temperature was controlled to 120° C.

The working solution discharged from a reactor was analyzed in the following manner, and as a result, it was apparent that the concentration of amyltetrahydroanthraquinone was 0.194 mol/liter and that of amylanthraquinone was 0.021 mol/liter. The amount of regenerated alkyltetrahydroanthraquinones was 0.021 mol/liter.

[Analysis of the working solution after the completion of the reaction]

The working solution discharged from the reactor was cooled by a cooling tube, sufficiently oxidized, washed with water, dehydrated, filtered, and then analyzed by liquid chromatography to measure the concentrations of various components.

The concentration of the anthrahydroquinones in the working solution was calculated on the basis of the amount of absorbed oxygen per unit volume of the working solution. Furthermore, the amount of alkylanthraquinones into which the alkyltetrahydroanthraquinones were converted was calculated by deducting the amount of the alkylanthraquinones regenerated from alkyloxyanthrones, from the increased amount of the alkylanthraquinones in the working solution after the reaction. The value obtained by this calculation will simply be called the regeneration of the alkyltetrahydroanthraquinones.

EXAMPLE 2

Reaction was carried out by the same procedure as in Example 1 except that there was used a working solution in which amyltetrahydroanthraquinone was partially reduced so that the concentration of amyltetrahydroanthrahydroquinone might be 0.080 mol/liter and that of alkyltetrahydroanthraquinones might be 0.145 mol/liter.

The working solution discharged from the reactor was analyzed in the same manner as in Example 1, and as a result, the concentration of amyltetrahydroanthraquinone was 0.196 mol/liter and that of amylanthraquinone was 0.010 mol/liter. The regeneration of the alkyltetrahydroanthraquinones was 0.010 mol/liter.

EXAMPLE 3

There was used a working solution obtained in an experimental device in which the working solution containing amylanthraquinone and amyltetrahydroanthraquinone as reaction media was alternately reduced and oxidized to produce hydrogen peroxide. In this working solution, the concentration of amyltetrahydroanthraquinone was 0.150 mol/liter, that of amyltetrahydroanthrahydroquinone was 0.05 mol/liter, that of amylanthraquinone was 0.580 mol/liter, that of amyloxyanthrone was 0.012 mol/liter, and that of amyltetrahydroanthraquinone epoxide was 0.010 mol/liter. In this working solution, solid components other than mentioned above were contained in an amount of about 10 wt% of the total solid components, but since they scarcely changed in this example, they will not particularly be referred to hereinafter. A reactor was filled with 300 ml of AA400G (14 to 48 mesh) made by Alcan Chemicals Co., Ltd. as a γ-alumina. After the reactor had sufficiently been purged with nitrogen, the working solution prepared above was fed at 220 ml/hr to carry out regeneration reaction. A reaction temperature was controlled to 120° C.

The regeneration reaction of the working solution was accomplished by feeding the working solution from bottom to top of the fixed bed type reactor filled with the γ-alumina. The fixed bed type reactor was made of stainless steel, and this reactor was fixed at upper and lower positions of its catalyst filling portion by a filter having a mesh size of about 20 μm. The reactor itself was also heated from the outside, but the working solution was previously heated up to a predetermined temperature and then introduced into the catalyst filling portion so that the temperature of the catalyst filling portion might be uniform as much as possible. Furthermore, the working solution to be fed was sufficiently nitrogen-sealed prior to its introduction into the reactor.

The working solution (after 24 hours had lapsed from the start of the reaction) discharged from the reactor was analyzed in the same manner as in Example 1. As a result, the concentration of amyltetrahydroanthraquinone was 0.188 mol/liter, that of amylanthraquinone was 0.607 mol/liter, and that of amyltetrahydroanthraquinone epoxide and amyloxyanthrone was 0.000 mol/liter. The regeneration of the alkyltetrahydroanthraquinones was 0.015 mol/liter.

EXAMPLE 4

Reaction was carried out by the same procedure as in Example 3 except that there was used a working solution in which the concentration of amyltetrahydroanthraquinone was 0.08 mol/liter, that of amyltetrahydroanthrahydroquinone was 0.12 mol/liter, that of amylanthraquinone was 0.580 mol/liter, that of amyloxyanthrone was 0.012 mol/liter, and that of amyltetrahydroanthraquinone epoxide was 0.010 mol/liter.

The working solution (after 24 hours had lapsed from the start of the reaction) discharged from a reactor was sufficiently oxidized and then analyzed in the same manner as in Example 1. As a result, the concentration of amyltetrahydroanthraquinone was 0.190 mol/liter, that of amylanthraquinone was 0.597 mol/liter, and that of amyltetrahydroanthraquinone epoxide and amyloxyanthrone was 0.000 mol/liter. The regeneration of the alkyltetrahydroanthraquinones was 0.005 mol/liter.

EXAMPLE 5

Reaction was carried out by the same procedure as in Example 3 except that a γ-alumina, Sunbead AN made by Shokubai Chemical Co., Ltd. was used as a catalyst.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.188 mol/liter, that of amylanthraquinone was 0.607 mol/liter, and that of amyltetrahydroanthraquinone epoxide and amyloxyanthrone was 0.000 mol/liter. The regeneration of the alkyltetrahydroanthraquinones was 0.015 mol/liter.

EXAMPLE 6

Reaction was carried out by the same procedure as in Example 3 except that a γ-alumina, KHD-24 made by Sumitomo Chemical Co., Ltd. was used as a catalyst.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.190 mol/liter, that of amylanthraquinone was 0.605 mol/liter, and that of amyltetrahydroanthraquinone epoxide and amyloxyanthrone was 0.000 mol/liter. The regeneration of the alkyltetrahydroanthraquinones was 0.013 mol/liter.

EXAMPLE 7

Reaction was carried out by the same procedure as in Example 1 except that a γ-alumina, GB-13 made by Mizusawa Chemical Co., Ltd. was used as a catalyst.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.190 mol/liter, that of amylanthraquinone was 0.605 mol/liter, and that of amyltetrahydroanthraquinone epoxide and amyloxyanthrone was 0.000 mol/liter. The regeneration of the alkyltetrahydroanthraquinones was 0.013 mol/liter.

COMPARATIVE EXAMPLE 1

Reaction was carried out by the same procedure as in Example 3 except that there was used a reduced working solution in which the concentration of amyltetrahydroanthraquinone was 0.35 mol/liter, that of amyltetrahydroanthrahydroquinone was 0.165 mol/liter, that of amylanthraquinone was 0.580 mol/liter, that of amyloxyanthrone was 0.012 mol/liter, and that of amyltetrahydroanthraquinone epoxide was 0.010 mol/liter.

The working solution (after 24 hours had lapsed from the start of the reaction) discharged from a reactor was sufficiently oxidized and then analyzed in the same manner as in Example 1. As a result, the concentration of amyltetrahydroanthraquinone was 0.185 mol/liter, that of amylanthraquinone was 0.593 mol/liter, and that of amyltetrahydroanthraquinone epoxide and amyloxyanthrone was 0.000 mol/liter. The regeneration of the alkyltetrahydroanthraquinones was 0.001 mol/liter.

COMPARATIVE EXAMPLE 2

Reaction was carried out by the same procedure as in Example 3 except that there was used a reduced working solution in which the concentration of amyltetrahydroanthraquinone was 0.000 mol/liter, that of amyltetrahydroanthrahydroquinone was 0.20 mol/liter, that of amylanthraquinone was 0.44 mol/liter, that of amylanthrahydroquinone was 0.14 mol/liter, that of amyloxyanthrone was 0.012 mol/liter, and that of amyltetrahydroanthraquinone epoxide was 0.010 mol/liter.

The working solution (after 24 hours had lapsed from the start of the reaction) discharged from a reactor was sufficiently oxidized and then analyzed in the same manner as in Example 1. As a result, the concentration of amyltetrahydroanthraquinone was 0.176 mol/liter, that of amylanthraquinone was 0.557 mol/liter, that of amyltetrahydroanthraquinone epoxide was 0.000, and that of amyloxyanthrone was 0.035 mol/liter. The regeneration of the alkyltetrahydroanthraquinones was 0.000 mol/liter.

EXAMPLE 8

Reaction was carried out by the same procedure as in Example 3 except that the reaction temperature of a working solution was 100° C.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.205 mol/liter, that of amylanthraquinone was 0.597 mol/liter, and that of amyltetrahydroanthraquinone epoxide and amyloxyanthrone was 0.000 mol/liter. The regeneration of the alkyltetrahydroanthraquinones was 0.005 mol/liter.

EXAMPLE 9

Reaction was carried out by the same procedure as in Example 3 except that the reaction temperature of a working solution was 80° C.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.206 mol/liter, that of amylanthraquinone was 0.594 mol/liter, that of amyltetrahydroanthraquinone epoxide was 0.005 mol/liter, and that of amyloxyanthrone was 0.000 mol/liter. The regeneration of the alkyltetrahydroanthraquinones was 0.002 mol/liter.

COMPARATIVE EXAMPLE 3

Reaction was carried out by the same procedure as in Example 3 except that the reaction temperature of a working solution was 30° C.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.200 mol/liter, that of amylanthraquinone was 0.587 mol/liter, that of amyltetrahydroanthraquinone epoxide was 0.010 mol/liter, and that of amyloxyanthrone was 0.005 mol/liter. The regeneration of the alkyltetrahydroanthraquinones was 0.000 mol/liter.

EXAMPLE 10

Reaction was carried out by the same procedure as in Example 3 except that the reaction temperature of a working solution was 60° C.

A working solution (after 24 hours had lapsed from the start of the reaction) discharged from a reactor was sufficiently oxidized and then analyzed in the same manner as in Example 1. As a result, the concentration of amyltetrahydroanthraquinone was 0.195 mol/liter, that of amylanthraquinone was 0.594 mol/liter, that of amyltetrahydroanthraquinone epoxide was 0.009 mol/liter, and that of amyloxyanthrone was 0.000 mol/liter. The regeneration of the alkyltetrahydroanthraquinones was 0.002 mol/liter.

EXAMPLE 11

Reaction was carried out by the same procedure as in Example 3 except that there was used a working solution in which the concentration of amyltetrahydroanthraquinone was 0.15 mol/liter, that of amyltetrahydroanthrahydroquinone was 0.05 mol/liter, that of amylanthraquinone was 0.532 mol/liter, that of amyloxyanthrone was 0.06 mol/liter, and that of amyltetrahydroanthraquinone epoxide was 0.010 mol/liter.

The working solution (after 24 hours had lapsed from the start of the reaction) discharged from a reactor was sufficiently oxidized and then analyzed in the same manner as in Example 1. As a result, the concentration of amyltetrahydroanthraquinone was 0.191 mol/liter, that of amylanthraquinone was 0.594 mol/liter, that of amyltetrahydroanthraquinone epoxide was 0.006 mol/liter, and that of amyloxyanthrone was 0.000 mol/liter. The regeneration of the alkyltetrahydroanthraquinones was 0.002 mol/liter.

EXAMPLE 12

A working solution was prepared in which the concentration of amyltetrahydroanthrahydroquinone was 0.337 mol/liter, that of amyltetrahydroanthraquinone was 0.000 mol/liter, and that of amyltetrahydrooxyanthrone was 0.063 mol/liter. In this example, AA400G (14 to 48 mesh) made by Alcan Chemicals Co., Ltd. was used as a γ-alumina. Next, 100 ml of the above-mentioned working solution was placed in a 200-ml flask, and the introduction of nitrogen was begun and the working solution was then heated up to 60° C. with stirring. When this working solution had reached 60° C., 10.0 g of the γ-alumina was fed, and reaction was carried out for 2 hours. Afterward, the working solution was sufficiently oxidized, washed with water, dehydrated, filtered, and then analyzed by liquid chromatography to measure the concentrations of various components. In consequence, the concentration of amyltetrahydroanthraquinone was 0.371 mol/liter, and that of amyltetrahydrooxyanthrone was 0.029 mol/liter.

In this connection, for the preparation of the working solution, a mixed solvent of 60 vol% of 1,2,4trimethylbenzene and 40 vol% of diisobutylcarbinol was used. Furthermore, the analysis of the oxidized solution by the liquid chromatography was carried out after all of alkyltetrahydroanthraquinones in the working solution at the start of the reaction had been reduced into alkyltetrahydroanthrahydroquinones. The concentration of anthrahydroquinones in the working solution was calculated on the basis of the amount of absorbed oxygen per unit volume of the working solution (the same shall apply hereinafter).

EXAMPLE 13

Reaction was carried out by the same procedure as in Example 12 except that there was used a working solution in which the concentration of amyltetrahydroanthrahydroquinone was 0.000 mol/liter, that of amyltetrahydroanthraquinone was 0.337 mol/liter, and that of amyltetrahydrooxyanthrone was 0.063 mol/liter. After the completion of the reaction, the concentrations of various components were measured. As a result, the concentration of amyltetrahydroanthraquinone was 0.390 mol/liter, that of amyltetrahydrooxyanthrone was 0.005 mol/liter, and that of amylanthraquinone was 0.003 mol/liter.

EXAMPLE 14

Reaction was carried out by the same procedure as in Example 12 except that there was used a working solution in which the concentration of amyltetrahydroanthrahydroquinone was 0.169 mol/liter, that of amyltetrahydroanthraquinone was 0.168 mol/liter, and that of amyltetrahydrooxyanthrone was 0.063 mol/liter. After the completion of the reaction, the concentrations of various components were measured. As a result, the concentration of amyltetrahydroanthraquinone was 0.382 mol/liter, and that of amyltetrahydrooxyanthrone was 0.017 mol/liter.

EXAMPLE 15

Reaction was carried out by the same procedure as in Example 12 except that there was used a working solution in which the concentration of amyltetrahydroanthrahydroquinone was 0.000 mol/liter, that of amyltetrahydroanthraquinone was 0.337 mol/liter and that of amyltetrahydrooxyanthrone was 0.063 mol/liter, and a reaction temperature was 80° C. After the completion of the reaction, the concentrations of various components were measured. As a result, the concentration of amyltetrahydroanthraquinone was 0.386 mol/liter, that of amyltetrahydrooxyanthrone was 0.007 mol/liter, and that of amylanthraquinone was 0.002 mol/liter.

EXAMPLE 16

Reaction was carried out by the same procedure as in Example 12 except that there was used a working solution in which the concentration of amyltetrahydroanthrahydroquinone was 0.051 mol/liter, that of amyltetrahydroanthraquinone was 0.286 mol/liter and that of amyltetrahydrooxyanthrone was 0.063 mol/liter, and a reaction temperature was 80° C. After the completion of the reaction, the concentrations of various components were measured. As a result, the concentration of amyltetrahydroanthraquinone was 0.383 mol/liter, that of amyltetrahydrooxyanthrone was 0.013 mol/liter, and that of amylanthraquinone was 0.002 mol/liter.

EXAMPLE 17

Reaction was carried out by the same procedure as in Example 12 except that there was used a working solution in which the concentration of amyltetrahydroanthrahydroquinone was 0.337 mol/liter, that of amyltetrahydroanthraquinone was 0.000 mol/liter and that of amyltetrahydrooxyanthrone was 0.063 mol/liter, and a reaction temperature was 80° C. After the completion of the reaction, the concentrations of various components were measured. As a result, the concentration of amyltetrahydroanthraquinone was 0.362 mol/liter, that of amyltetrahydrooxyanthrone was 0.041 mol/liter, and that of amylanthraquinone was 0.000 mol/liter.

EXAMPLE 18

Reaction was carried out by the same procedure as in Example 12 except that there was used a working solution in which the concentration of amyltetrahydroanthrahydroquinone was 0.000 mol/liter, that of amyltetrahydroanthraquinone was 0.337 mol/liter and that of amyltetrahydrooxyanthrone was 0.063 mol/liter, and a reaction temperature was 100° C. After the completion of the reaction, the concentrations of various components were measured. As a result, the concentration of amyltetrahydroanthraquinone was 0.373 mol/liter, that of amyltetrahydrooxyanthrone was 0.011 mol/liter, and that of amylanthraquinone was 0.014 mol/liter.

EXAMPLE 19

Reaction was carried out by the same procedure as in Example 12 except that there was used a working solution in which the concentration of amyltetrahydroanthrahydroquinone was 0.182 mol/liter, that of amyltetrahydroanthraquinone was 0.155 mol/liter and that of amyltetrahydrooxyanthrone was 0.063 mol/liter, and a reaction temperature was 100° C. After the completion of the reaction, the concentrations of various components were measured. As a result, the concentration of amyltetrahydroanthraquinone was 0.363 mol/liter, that of amyltetrahydrooxyanthrone was 0.033 mol/liter, and that of amylanthraquinone was 0.004 mol/liter.

EXAMPLE 20

Reaction was carried out by the same procedure as in Example 12 except that there was used a working solution in which the concentration of amyltetrahydroanthrahydroquinone was 0.000 mol/liter, that of amyltetrahydroanthraquinone was 0.337 mol/liter and that of amyltetrahydrooxyanthrone was 0.063 mol/liter, and a reaction temperature was 120° C. After the completion of the reaction, the concentrations of various components were measured. As a result, the concentration of amyltetrahydroanthraquinone was 0.339 mol/liter, that of amyltetrahydrooxyanthrone was 0.023 mol/liter, and that of amylanthraquinone was 0.039 mol/liter.

EXAMPLE 21

Reaction was carried out by the same procedure as in Example 12 except that there was used a working solution in which the concentration of amyltetrahydroanthrahydroquinone was 0.167 mol/liter, that of amyltetrahydroanthraquinone was 0.170 mol/liter and that of amyltetrahydrooxyanthrone was 0.063 mol/liter, and a reaction temperature was 120° C. After the completion of the reaction, the concentrations of various components were measured. As a result, the concentration of amyltetrahydroanthraquinone was 0.339 mol/liter, that of amyltetrahydrooxyanthrone was 0.043 mol/liter, and that of amylanthraquinone was 0.020 mol/liter.

COMPARATIVE EXAMPLE 4

Reaction was carried out by the same procedure as in Example 12 except that there was used a working solution in which the concentration of amyltetrahydroanthrahydroquinone was 0.337 mol/liter,-that of amyltetrahydroanthraquinone was 0.000 mol/liter and that of amyltetrahydrooxyanthrone was 0.063 mol/liter, and a reaction temperature was 120° C. After the completion of the reaction, the concentrations of various components were measured. As a result, the concentration of amyltetrahydroanthraquinone was 0.327 mol/liter, and that of amyltetrahydrooxyanthrone was 0.063 mol/liter.

COMPARATIVE EXAMPLE 5

Reaction was carried out by the same procedure as in Comparative Example 4 except that a reaction temperature was 140° C. After the completion of the reaction, the concentrations of various components were measured. As a result, the concentration of amyltetrahydroanthraquinone was 0.327 mol/liter, and that of amyltetrahydrooxyanthrone was 0.074 mol/liter.

COMPARATIVE EXAMPLE 6

Reaction was carried out by the same procedure as in Example 12 except that there was used a working solution in which the concentration of amyltetrahydroanthrahydroquinone was 0.237 mol/liter, that of amyltetrahydroanthraquinone was 0.100 mol/liter and that of amyltetrahydrooxyanthrone was 0.063 mol/liter, and a reaction temperature was 150° C. After the completion of the reaction, the concentrations of various components were measured. As a result, the concentration of amyltetrahydroanthraquinone was 0.320 mol/liter, that of amyltetrahydrooxyanthrone was 0.064 mol/liter, and that of amylanthraquinone was 0.014 mol/liter.

COMPARATIVE EXAMPLE 7

Reaction was carried out by the same procedure as in Comparative Example 4 except that a reaction temperature was 100° C. After the completion of the reaction, the concentrations of various components were measured. As a result, the concentration of amyltetrahydroanthraquinone was 0.347 mol/liter, and that of amyltetrahydrooxyanthrone was 0.053 mol/liter.

What is claimed is:

1. A method for regenerating a working solution containing an anthraquoinone dissolved in at least one solvent selected from the group consisting of trimethylbenzene and diisobutylcarbinol, from a process for producing hydrogen peroxide by repeatedly reducing and oxidizing the working solution, wherein the antraquinone in the working solution comprises at least one alkyltetrahydroanthraquinone selected from the group consisting of amyltetrahydroanthraquinone, ethyltetrahydroanthraquinone and t-butyltetrahydroanthraquinone, the method comprising bringing the working solution into contact with a catalyst comprising a γ-alumina and having a particle size of 8 to 100 mesh at a treatment temperature of 20° to 150° C. under conditions that a concentration h (mol/liter) of the at least one alkyltetrahydroanthrahydroquinone in the working solution before the contact with the catalyst satisfies the following equation:

$$(0018\times t-0.0285)\times h<0.05$$

wherein t is the treatment temperature (°C.), to convert any alkyltetrahydrooxyanthrones in the working solution into alkyltetrahydroanthrahydroquinones.

2. The method according to claim 1 wherein the concentration h (mol/liter) of the at least one alkyltetrahydroanthrahydroquinone in the working solution before the contact with the catalyst is 0.15 mol/liter or less and satisfies the following equation:

$$(0.0018\times t-0.0285)\times h<0.02,$$

wherein t is the treatment temperature (°C.).

3. The method according to claim 1, wherein the catalyst has a particle size of 8 to 100 mesh.

4. The method according to claim 3, wherein the method is carried out in a stirrer-equipped reactor, a fixed bed reaction or a fluidized bed reactor.

5. The method according to claim 1, wherein the working solution which is brought into contact with the catalyst comprises amyltetrahydroanthraquinone and amyltetrahydrooxyanthrone.

6. The method according to claim 5, wherein said at least one solvent comprises 1,2,4-trimethylbenzene and diisobutylcarbinol.

7. The method according to claim 6, wherein the treatment temperature is 60° C.

8. The method according to claim 6, wherein the treatment temperature is 100° C.

9. The method according to claim 6, wherein the treatment temperature is 120° C.

* * * * *